United States Patent
Hickle

(10) Patent No.: US 7,316,231 B2
(45) Date of Patent: Jan. 8, 2008

(54) RESUSCITATION KIT SYSTEM AND METHOD AND PRE-USE PROTOCOLS FOR A SEDATION AND ANALGESIA SYSTEM

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 683 days.

(21) Appl. No.: 10/637,049

(22) Filed: Aug. 8, 2003

(65) Prior Publication Data
US 2004/0084047 A1   May 6, 2004

Related U.S. Application Data

(60) Provisional application No. 60/401,785, filed on Aug. 8, 2002.

(51) Int. Cl.
*A61M 16/00* (2006.01)

(52) U.S. Cl. ............ 128/203.13; 600/300; 128/204.23

(58) Field of Classification Search .......... 128/203.12, 128/203.13, 203.15, 203.14, 200.24, 204.18, 128/204.21, 204.23; 600/300; 604/131, 604/151; 700/231, 232, 233, 234, 237; 221/2
See application file for complete search history.

(56) References Cited

U.S. PATENT DOCUMENTS

| | | | |
|---|---|---|---|
| 4,266,669 A * | 5/1981 | Watson ....................... 206/564 | |
| 4,695,954 A | 9/1987 | Rose et al. | |
| 5,848,593 A | 12/1998 | McGrady et al. | |
| 6,112,502 A * | 9/2000 | Frederick et al. ............. 53/411 |
| 6,832,200 B2 * | 12/2004 | Greeven et al. ................ 705/3 |
| 2003/0051737 A1 * | 3/2003 | Hickle et al. ................ 128/923 |
| 2003/0079746 A1 * | 5/2003 | Hickle ................... 128/203.12 |
| 2003/0135087 A1 * | 7/2003 | Hickle et al. ................. 600/26 |
| 2003/0176774 A1 * | 9/2003 | Hickle et al. ............... 600/300 |
| 2003/0209242 A1 * | 11/2003 | Hickle ................... 128/203.12 |
| 2003/0217747 A1 * | 11/2003 | Hickle et al. .......... 128/203.12 |
| 2004/0034287 A1 * | 2/2004 | Hickle ........................ 600/300 |
| 2004/0039257 A1 * | 2/2004 | Hickle ........................ 600/300 |
| 2004/0129271 A1 * | 7/2004 | Hickle ................... 128/204.23 |
| 2004/0129273 A1 * | 7/2004 | Hickle ................... 128/207.14 |
| 2004/0133187 A1 * | 7/2004 | Hickle ..................... 604/890.1 |

OTHER PUBLICATIONS

International Search Report for International Application No. PCT/US03/24696 dated Mar. 10, 2004.

* cited by examiner

*Primary Examiner*—Steven O. Douglas
(74) *Attorney, Agent, or Firm*—Hogan & Hartson LLP

(57) ABSTRACT

The present invention provides a sedation and analgesia system having an emergency medical kit, where the medical kit is designed to meet the specific needs of medical emergencies related to the delivery of sedatives, analgesics, and/or amnestics. The invention further provides a sedation and analgesia system with an emergency medical kit having policies along with automated and semi-automated pre-use checks necessary to ensure that components of the kit are present, functioning properly, and that perishable components within the kit have not expired.

20 Claims, 10 Drawing Sheets

Sedation and Analgesia System
Emergency Medical Supply Checklist

| | Present? | Functioning Properly? | Unexpired? | Pressurized? |
|---|---|---|---|---|
| Supplies for Emergency Back-Up Controlled Ventilation: | | | | |
| 144 — Oxygen Cylinder with Toggle Handle | X | X | N/A | N/A |
| 145 — Oxygen Tank Pressure Gauge | X | X | N/A | N/A |
| 146 — Oxygen Flow Regulator | X | X | N/A | N/A |
| 147 — Oxygen Tubing | X | X | N/A | N/A |
| 148 — Ambu Bag (Pediatric) | X | X | N/A | N/A |
| 149 — Ambu Bag (Adult) | X | X | N/A | N/A |
| 150 — Mask (Pediatric) | X | X | N/A | N/A |
| 151 — Mask (Adult) | X | X | N/A | N/A |
| 152 — Strap for Oxygen Mask | X | X | N/A | N/A |
| 153 — Non-Rebreathing Oxygen Mask | X | X | N/A | N/A |
| Supplies for Emergency Back-Up Monitoring Capability: | | | | |
| 154 — Battery Operated Pulse Oximeter | X | X | N/A | N/A |
| 155 — Sphygmomanometer | X | X | N/A | N/A |
| 156 — Stethoscope | X | X | N/A | N/A |
| Supplies for Emergency Back-Up Emesis Aspirator: | | | | |
| 157 — Manually Operated Emesis Aspirator | X | X | N/A | N/A |

FIG. 3A

Sedation and Analgesia System
Emergency Medical Supply Checklist

| | Present? | Functioning Properly? | Unexpired? | Pressurized? |
|---|---|---|---|---|
| Supplies for Emergency Airway Management and Intubation: | | | | |
| Oral Airway (Small) | X | | | N/A |
| Oral Airway (Medium) | X | X | N/A | N/A |
| Oral Airway (Large) | X | | | N/A |
| Nasal Airway | X | X | N/A | N/A |
| Laryngoscope | X | X | N/A | N/A |
| Extra Bulb for Laryngoscope | X | X | N/A | N/A |
| Extra Batteries for Laryngoscope | X | X | N/A | N/A |
| Laryngoscope Blades: | | | | |
|   MAC 2 | | | | |
|   MAC 3 | X | X | N/A | N/A |
|   MAC 4 | | | | |
|   Miller 2 | | | | |
| Tracheal Tubes (Cuffed): | | | | |
|   5mm | | | | |
|   6mm | X | X | N/A | N/A |
|   7mm | | | | |
|   8mm | | | | |

158 — Oral Airway rows
159 — Nasal Airway
160 — Laryngoscope
161 — Extra Bulb for Laryngoscope
162 — Extra Batteries for Laryngoscope
163 — Laryngoscope Blades
164 — Tracheal Tubes

FIG. 3B

Sedation and Analgesia System
Emergency Medical Supply Checklist

| | Present? | Functioning Properly? | Unexpired? | Pressurized? |
|---|---|---|---|---|
| Supplies for Emergency Airway Management and Intubation: (cont'd) | | | | |
| Tracheal Tubes (Uncuffed): | | | | |
| 2mm | | | | |
| 2.5mm | | | | |
| 3mm | | | | |
| 3.5mm | | | | |
| 4mm | X | X | N/A | N/A |
| 4.5mm | | | | |
| 5mm | | | | |
| 5.5mm | | | | |
| 6mm | | | | |
| Stylet | X | X | X | N/A |
| Adhesive Tape | X | X | X | N/A |

| Vasopressors: | | | | |
|---|---|---|---|---|
| Ephedrine | X | N/A | X | N/A |
| Neosynephrine | X | N/A | X | N/A |
| Epinephrine | X | N/A | X | N/A |

FIG. 3C

Sedation and Analgesia System
Emergency Medical Supply Checklist

| | Present? | Functioning Properly? | Unexpired? | Pressurized? |
|---|---|---|---|---|
| Rate Stimulation Drugs: | | | | |
| 171 — Atropine | X | N/A | X | N/A |
| Drugs for Treatment of Anaphylaxis: | | | | |
| 172 — Diphenhydramine | X | N/A | X | N/A |
| 173 — Glucocorticoid | X | N/A | X | N/A |
| Bronchodilators: | | | | |
| 174 — Aminophylline | X | N/A | X | N/A |
| 175 — Ventolin Inhaler | X | N/A | X | N/A |
| Anti-Arrhythmic Drugs: | | | | |
| 176 — Digoxin | X | N/A | X | N/A |
| 177 — Lidocaine (100 mg) | X | N/A | X | N/A |
| 178 — Procainamide | X | N/A | X | N/A |
| 179 — Verapamil | X | N/A | X | N/A |
| Drugs for Myocardial Ischemia: | | | | |
| 180 — Nitroglycerine (Sublingual or Patch) | X | N/A | X | N/A |
| 181 — Nifedipine Capsules | X | N/A | X | N/A |

FIG. 3D

Sedation and Analgesia System
Emergency Medical Supply Checklist

| | Present? | Functioning Properly? | Unexpired? | Pressurized? |
|---|---|---|---|---|
| Cardiopulmonary Resuscitation Drugs: | | | | |
| 182 — Calcium Chloride | X | N/A | X | N/A |
| 183 — Sodium Bicarbonate | X | N/A | X | N/A |
| Pharmacological Antagonists: | | | | |
| 184 — Naloxone | X | N/A | X | N/A |
| 185 — Flumazenil | X | N/A | X | N/A |
| Miscellaneous: | | | | |
| 186 — Dextrose | X | N/A | X | N/A |
| 187 — Furosemide | X | N/A | X | N/A |
| 188 — I.V. Catheter | X | X | N/A | N/A |
| 189 — I.V. Tubing | X | X | N/A | N/A |
| 190 — Syringes | X | X | N/A | N/A |
| 191 — Needles | X | X | N/A | N/A |
| 192 — Alcohol Swabs | X | X | N/A | N/A |

FIG. 3E

RESUSCITATION KIT SYSTEM AND METHOD AND PRE-USE PROTOCOLS FOR A SEDATION AND ANALGESIA SYSTEM

CROSS REFERENCE TO RELATED APPLICATIONS

This application claims priority under 35 U.S.C. § 119(e) to U.S. Provisional Patent Application No. 60/401,785, "Resuscitation Kit System and Method and Pre-Use Protocols for a Sedation and Analgesia System," filed Aug. 8, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates, in general, to emergency medical kits and pre-use checks and, more particularly, to emergency medical kits and pre-use checks associated with sedation and analgesia systems.

2. Description of the Related Art

A sedation and analgesia system has been developed to provide patients undergoing painful, uncomfortable or otherwise frightening (anxiety inspiring) medical or surgical procedures with a means for receiving sedative, analgesic, and/or amnestic drugs safely in a way that reduces the risk of overmedication with or without the presence of a licensed anesthesia provider. Due to significant advances in technology, the sedation and analgesia system may be safer for use in hospital and ambulatory environments and may be operated by individuals other than trained anesthesiologists such as, for example, C.R.N.A.'s, trained physicians, or other trained operators. The sedation and analgesia system has gone far to meet the needs of practitioners who are unable to schedule anesthesia providers for every procedure where safe and effective sedation and analgesia could substantially mitigate the effects of fear and pain. The advent of a sedation and analgesia system devoted to these purposes provides these individuals with a drug delivery system integrated into a patient monitoring system that decreases the cognitive and manual workload required with the operation of anesthesia machines, yet keeps the clinician in the loop of patient management. The clinician maintains ultimate decision making responsibility following a "clinician knows best" philosophy. This advanced technology allows for the sedation and analgesia system to be operated at drug level effects less than general anesthesia without an anesthesia provider, providing the patient with a cost-effective and readily available means of sedation, amnesia, and/or analgesia.

Due to the semi-automated nature of the sedation and analgesia system, sedatives, analgesics, and/or amnestics may be administered to patients outside of a hospital environment by non-anesthetist clinicians. Though the flexible use of such a system allows sedation, analgesia, and/or amnesia drugs to be administered in a wide variety of medical environments, many of these environments may not be equipped with the proper equipment and/or procedures to ensure patient safety during a medical emergency. For example, most operating rooms carry in-room suction equipment and they have well-established procedures for ensuring this equipment is ready to use in the event of life-threatening emesis with a high risk of pulmonary acid aspiration; prevention of which requires immediate oral and laryngeal suctioning. Many ambulatory environments where sedation and analgesia may be administered may not have the proper suction apparatus or the procedures for ensuring its immediate availability and proper function.

Similarly, most operating rooms have emergency medical equipment, supplies, and pharmaceutical agents located within close proximity to the procedural rooms. Further, operating rooms have policies and procedures ensuring that these emergency support systems are properly stocked and functional. Many procedure environments outside of the operating room do not stock all of the necessary emergency resuscitation equipment for treatment of sedation and analgesia adverse events, much less, have procedures for ensuring their presence and function. Though Joint Commission on Accreditation of Healthcare Organizations (JCAHO) regulations require a variety of general emergency medical supplies to be present in both hospitals and ambulatory environments, such kits may be large and bulky and may not be tailored to the specific needs of patients experiencing a medical emergency as a result of the delivery of sedative, analgesic, and/or amnestic drugs. The need has therefore arisen for an emergency medical kit in association with quality assurance procedures tailored specifically for medical emergencies involving a sedation and analgesia system.

Further, requiring clinicians to account for each additional emergency medical supply not present in a standard "crash" cart needed for procedures involving a sedation and analgesia system may require a great deal of time, where time between procedures may be at a premium. Supplies for a medical emergency may be present in varying degrees in medical environments outside the operating room, however the need exists for an efficient method and system of ensuring that all the necessary supplies are present to handle a medical emergency resulting from the delivery of sedatives, analgesics, and/or amnestics.

A number of resuscitation kits have been developed, such as those produced by Banyan International Corporation, for placement in a wide variety of locations such as airplanes and hotel lobbies, where such kits contain medical supplies that may be used in the event of a medical emergency. These kits are generally designed for use by a wide variety of individuals with a wide variety of skill levels from lay people who may administer basic first aid to fully trained intensive care physicians. Most existing kits are geared for a wide spectrum of care from first aid and basic life support to advanced cardiac life support (ACLS). When supplies from such kits are used during medical emergencies depleted, disabled, or contaminated supplies may not be replaced, which may result in the subsequent use of a kit that is missing necessary supplies or contains contaminated supplies. Further, there are generally no means to ensure that missing or expired drugs and/or non-functional equipment are replaced, potentially endangering recipients of the expired supplies. The need has therefore arisen for a method of ensuring that emergency medical supplies are present in the event of a medical emergency involving a sedation and analgesia system, that equipment is present and in full working order, and that emergency drugs are available and have not expired.

Medical kits designed for pulmonary and cardiac arrest are often found in hospital wards, where such kits generally carry a vast array of equipment and are mounted on wheels due to their large size. Such kits also involve a series of pre-use protocols to ensure that supplies contained within the kit are present, in working order, and have not expired. One example of these protocols is a supply checklist, where the checklist contains all of the required equipment and drugs for the kit and where each element of the kit may be checked off as it is determined to be present, functioning, and not expired. Such checklists are generally performed following the use of the "crash" cart and after a predetermined period of non-use, where expired supplies and depleted supplies are replaced before use of the kit is permitted. A further required procedure for many such kits involves the use of tamper evident seals, where a tamper evident seal may be placed on the kit following the restocking of the kit and the checklist procedure. Many tamper evident seals are marked with the date the checklist procedure was performed and must be broken for the kit to be used. Such pre-use checks have been effective in maintaining the quality of large in-house medical kits, however the large size of such kits generally limits their presence to a single kit per ward, and the vast quantity of equipment and drugs present in such kits may make finding needed supplies an inefficient and time consuming process. The need has therefore arisen for a readily available emergency medical kit that contains medical supplies specifically tailored to medical emergencies involving a sedation and analgesia system, where excess supplies unrelated to medical emergencies involving the delivery of sedatives, analgesics, and/or amnestics may be eliminated. The need further exists for emergency kits designed for, and integrated with, a sedation and analgesia system that has pre-use checks and procedures to ensure that required medical supplies are present, in working order, and have not expired.

Though JCAHO and other regulatory agencies use a number of policies and procedures to ensure that emergency medical kits employed in hospitals and ambulatory medical environments are present and functional, such policies and procedures do not extend to emergency medical kits specifically designed for a sedation and analgesia system. The need has therefore arisen for policies and procedures incorporated into a sedation and analgesia system that ensure the proper functionality of the system, that the necessary components of the system are present, and that emergency medical supplies associated with the system are present, functioning, and not expired. Due to the potentially time consuming nature of checking all components of a sedation and analgesia system and emergency medical supplies associated with such a system, the need has further arisen for pre-use checks and procedures that are efficient yet comprehensive.

BRIEF SUMMARY OF THE INVENTION

The present invention provides a sedation and analgesia system having an emergency medical kit, where the medical kit is designed to meet the specific needs of medical emergencies related to the delivery of sedatives, analgesics, and/or amnestics. The invention further provides a sedation and analgesia system with an emergency medical kit having policies and pre-use checks necessary to ensure that components of the kit are present, functioning properly, and that drugs and perishable components within the kit have not expired. The present invention even further provides an emergency medical kit for a sedation and analgesia system that is integrated with policies and procedures which require restocking and reevaluation of the kit after use or after a pre-determined period of non-use, where the kit may not be used until the policies and procedures have been adhered to. The invention also provides a sedation and analgesia system and emergency medical kit that have automated and/or semi-automated pre-use checks which efficiently ensure that the system and emergency medical kit are functioning properly and contain the proper components.

BRIEF DESCRIPTION OF THE DRAWINGS

FIGS. 3A-E illustrate a checklist of one embodiment of the present invention that is used to ensure the presence and functionality of supplies associated with an emergency medical kit;

DETAILED DESCRIPTION OF THE INVENTION

Figure 1:
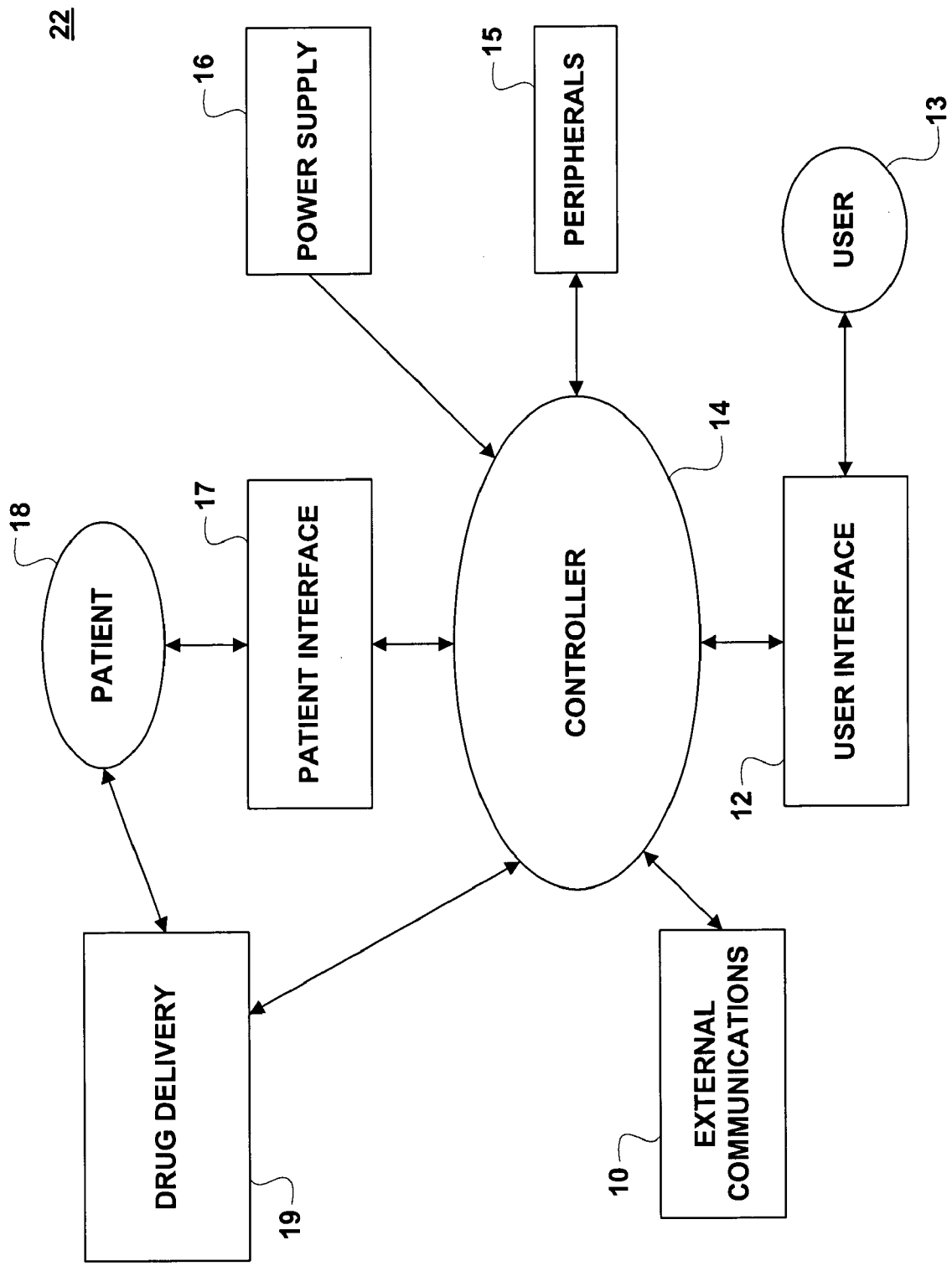
FIG. 1 illustrates a block diagram of one embodiment of a sedation and analgesia system for use with the present invention.

FIG. 1 illustrates a block diagram of one embodiment of a sedation and analgesia system 22 having user interface 12, software controlled controller 14, peripherals 15, power supply 16, external communications 10, patient interface 17, and drug delivery 19, where sedation and analgesia system 22 is operated by user 13 in order to provide sedation and/or analgesia to patient 18. An example of sedation and analgesia system 22 is disclosed and enabled by U.S. patent application Ser. No. 09/324,759, filed Jun. 3, 1999 which is herein incorporated by reference in its entirety. Embodiments of user interface 12 are disclosed and enabled by U.S. patent application Ser. No. 10/285,689, filed Nov. 1, 3002, which is herein incorporated by reference in its entirety.

Figure 2:
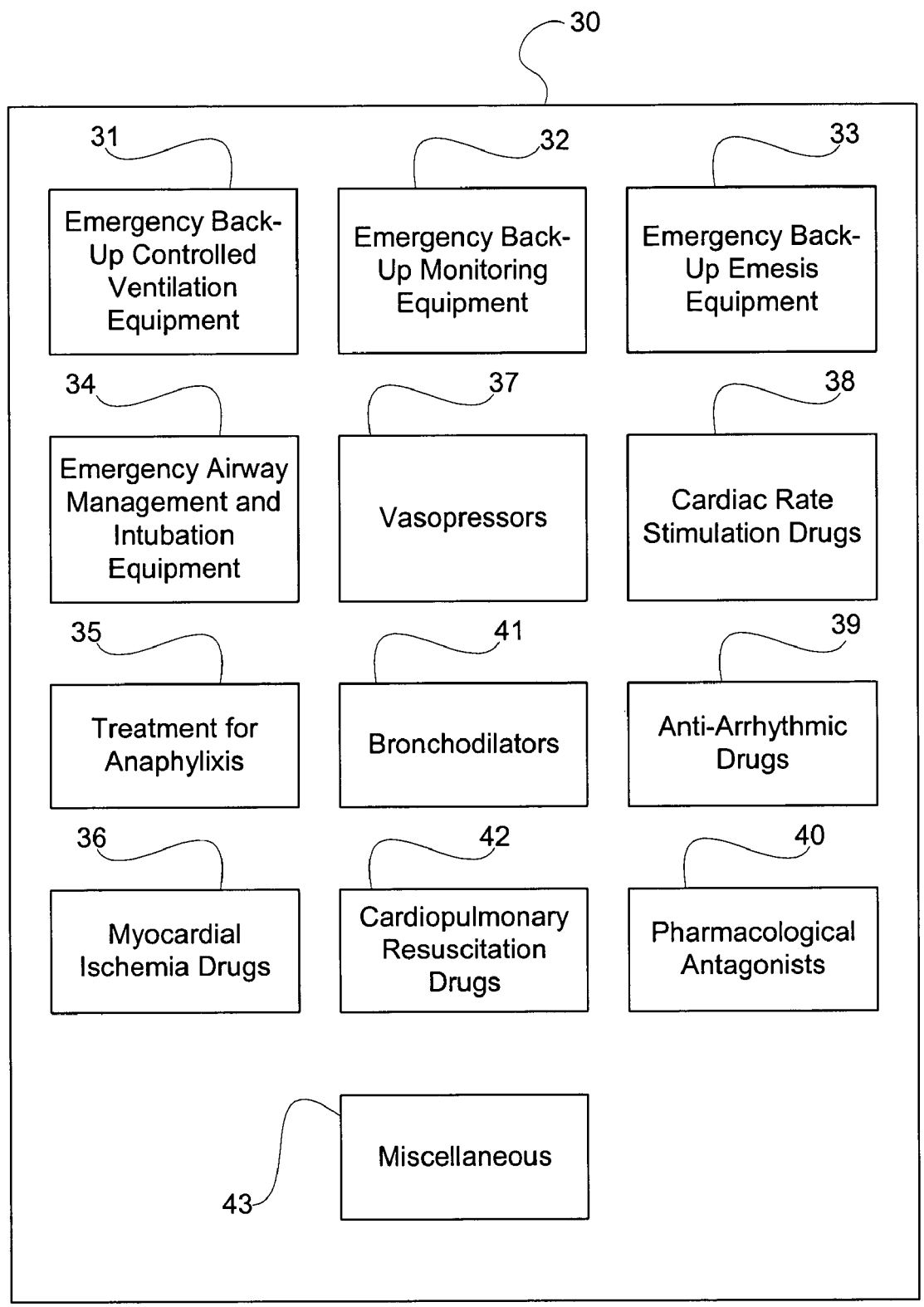
FIG. 2 illustrates a block diagram depicting one embodiment of an emergency medical kit for use with a sedation and analgesia system of the present invention.

FIG. 2 illustrates one embodiment of an emergency medical kit 30 particularly adapted to and integrated with sedation and analgesia system 22. Emergency medical kit 30 may be permanently affixed to, detachably coupled to, or positioned in close proximity to sedation and analgesia system 22, where emergency medical kit 30 may be used in the event of a medical emergency involving the use of sedation and analgesia system 22. Emergency medical kit 30 may be any suitable receptacle for holding emergency medical supplies such as, for example, a briefcase, drawer or cart. Emergency medical kit 30 may further include foam padding, injection molding, and/or other suitable insulation/shock absorbent material that may encase and/or support supplies within the kit 30 in order to prevent the movement and/or breakage of such supplies. Emergency medical kit 30 may be constructed from any suitable material such as, for example, acrylonatrile butadeine styrene (ABS), and may have a combination lock, key lock, clasp lock, or other suitable secure closure mechanism.

Emergency medical kit 30 may also include emergency back-up ventilation equipment 31. Emergency back-up ventilation equipment 31 may include an oxygen cylinder with toggle handle 144, an oxygen tank pressure gauge 145, an oxygen flow regulator 146, oxygen tubing 147, a pediatric ambu bag 148, an adult ambu bag 149, a pediatric mask 150, an adult mask 151, a strap 152 for an oxygen mask, and/or a non-rebreathing oxygen mask 153, among other items. Due to the respiratory depressant nature of many sedatives, analgesics, and amnestics, the present invention contemplates providing any suitable emergency supplies necessary to ensure patient safety in the event of a medical emergency related to the delivery of such drugs.

Emergency medical kit 30 may further include emergency back-up monitoring equipment 32, where emergency back-up monitoring equipment 32 may include a battery operated pulse oximeter 154, a sphygmomanometer 155, a stethoscope 156, and/or any other supplies suitable for providing back-up patient monitoring in the event of a sedation and analgesia system 22 failure. Many monitoring systems used with sedation and analgesia system 22 such as, for example, a pulse oximeter, may be powered by and incorporated directly into sedation and analgesia system 22. In the event of a power failure or system malfunction, the use of monitoring devices that are incorporated into sedation and analgesia system 22 may be disrupted. In order to ensure that critical patient parameters may still be monitored if such an event occurs, emergency medical kit 30 may contain monitoring supplies such as, for example, battery operated pulse oximeter 154, that are capable of providing the continuous monitoring of a patient in the event that sedation and analgesia system 22 becomes unavailable.

Emergency medical kit 30 may also include emergency back-up emesis equipment 33, where emergency back-up emesis equipment 33 may include a manually operated emesis aspirator 157 and/or other suitable equipment for providing aspiration in the event that in-house aspiration equipment such as, for example, hospital wall suction, is unavailable or fails. Due to the wide variety of environments in which sedation and analgesia system 22 may be operated where wall suction may be unavailable, such as ambulatory medical centers, the present invention contemplates providing back-up emesis equipment.

Emergency medical kit 30 may further include emergency airway management and intubation equipment 34, where emergency airway management and intubation equipment 34 may include, among other items, airway devices such as oral airways 158, a nasal airway 159, a laryngoscope 160, an extra bulb 161 for laryngoscope 160, extra batteries 162 for laryngoscope 160, laryngoscope blades 163, cuffed tracheal tubes 164, uncuffed tracheal tubes 165, a stylet 166, and/or adhesive tape 167. The present invention contemplates providing a wide spectrum of medical supplies to account for the wide spectrum of varied patient parameters. For example, the present invention comprises providing a plurality of oral airways 158 of varying size, a plurality of laryngoscope blades 163 of varying size, a plurality of uncuffed tracheal tubes 165 of varying size, and/or a plurality of cuffed tracheal tubes 164 of varying size. The spectrum of medical supplies included in medical kit 30 may also include supplies intended for use in pediatrics as well as supplies intended for use on adults in an emergency.

Emergency medical kit 30 may further include vasopressors 37, where vasopressors 37 may be used in the event of cardiac arrest, allergic reactions including anaphylaxis and/or associated hypotension. Any suitable drug characterized as a vasopressor such as, for example, ephedrine 168, neosynephrine 169, and epinephrine 170, may be incorporated into emergency medical kit 30. Emergency medical kit 30 also may include cardiac rate stimulation drugs 38, where cardiac rate stimulation drugs 38 comprise atropine 171 and/or any other suitable rate stimulation drug. Immediate access to such drugs is desirable because bradycardia may occur rapidly from multiple causes such as vagal stimulation related to valsalva, gastric distention, and underlying heart disease during sedation and analgesia. The close proximity of emergency medical kit 30 to sedation and analgesia system 22 and the patient ensures that access to such drugs is fast and efficient.

Emergency medical kit 30 may include treatment for anaphylaxis 35, where anaphylaxis generally represents an immunoglobulin E (IgE) acute mediated systemic reaction following antigen exposure in a sensitized individual. Treatment for anaphylaxis 35 may comprise a number of treatment drugs such as, for example, diphenhydramine 172 and glucocorticoid 173. Emergency medical kit 30 may further include bronchodilators 41, where bronchodilators are drugs that result in increased bronchial dilation and increased bronchial airflow thereby increasing forced expiratory volume per 1 sec. ($FEV_1$). The present invention contemplates the incorporation of any suitable bronchodilator such as, for example, aminophylline 174 and/or a ventolin inhaler 175, into emergency medical kit 30.

Emergency medical kit 30 may include anti-arrhythmia drugs 39 such as, for example, digoxin 176, lidocaine 177, procainamide 178, and/or verapamil 179. Cardiac arrhythmias may be atrial or ventricular with varying causality including hypoxia, electrolyte disorders, conduction abnormalities, and coronary artery disease, and may require immediate access to a wide spectrum of anti-arrhythmic drugs depending on the causation of the arrhythmic condition. Emergency medical kit 30 may also include myocardial ischemia drugs 36 such as, for example, a nitroglycerine patch 180, sublingual nitroglycerine 180, and/or nifedipine capsules 181. Myocardial ischemia results from inadequate oxygenation relative to tissue demand, and thus is related to decreased oxygen supply, increased oxygen demand, or both. Myocardial ischemia drugs may increase oxygen delivery with coronary artery vasodilatation and decrease consumption including afterload reduction. Emergency medical kit 30 may further include cardiopulmonary resuscitation drugs 42, such as, for example, calcium chloride 182 and/or sodium bicarbonate 183.

Emergency medical kit 30 may include pharmacological antagonists 40, where pharmacological antagonists generally diminish the effects of administered drugs by competitive inhibition. Any suitable pharmacological antagonist may be incorporated into emergency medical kit 30 such as, for example, naloxone 184 (reverses the effects of opioids) and flumazenil 185 (reverses the effects of benzodiazepines).

Emergency medical kit 30 may further include miscellaneous items 43, where miscellaneous items 43 may be any suitable supply or drug beneficial in remedying a medical emergency resulting from the use of a sedation and analgesia system. Examples of miscellaneous items 43 include drugs such as dextrose 186, which may be administered if a severely hypoglycemic condition arises in a patient, and furosemide 187 which may be administered in the event of a patient suffering from congestive heart failure or pulmonary edema. Further examples of miscellaneous items 43 include intravenous (I.V.) catheters 188, I.V. tubing 189, syringes 190, needles 191, and alcohol swabs 192.

FIGS. 3A-E illustrate one embodiment of a sedation and analgesia system emergency medical supply checklist 100, herein referred to as checklist 100, where checklist 100 comprises supply list 110. In one embodiment of the present invention, supply list 110 comprises listing all supplies required for emergency medical kit 30, where such supplies may be categorized or grouped by function and/or classification and/or adverse event. In one embodiment of the present invention, supply list 110 is subdivided into emergency back-up controlled ventilation equipment 31, emergency back-up monitoring equipment 32, emergency back-up emesis equipment 33, emergency airway management and intubation equipment 34, vasopressors 37, cardiac rate stimulation drugs 38, treatment for anaphylaxis 35, bronchodilators 41, anti-arrhythmic drugs 39, myocardial ischemia drugs 36, cardiopulmonary resuscitation drugs 42, pharmacological antagonists 40; and miscellaneous items 43. Following each subdivision, supplies categorized by that subdivision may be listed. For example, following the vasopressors 37 subdivision of supply list 110 all vasopressors required to be present in emergency medical kit 30 may be listed such as, for example, ephedrine 168, neosynephrine 169, and epinephrine 170. Examples of supplies that may be required to be present in the subdivisions are listed where the equipment of those subdivisions are described in relation to FIG. 2 above. The illustrated means of organizing checklist 100 is disclosed by way of example only and a plurality of suitable means of organizing checklist 100 is contemplated by the present invention. Further, a number of supplies for emergency medical kit 30 may be listed in multiple categories, where any suitable organization of such supplies is in accordance with the present invention.

Checklist 100 further may include, for example, at least one of column 115, column 120, column 125, and/or column 130. Column 115 may, in one embodiment of the present invention, contain the designation "Present?", where the individual or system performing the checklist procedure may be required to place an "X" or other suitable designation in column 115 to represent that a supply of supply list 110 is present in emergency medical kit 30. For example, the individual or system performing the checklist procedure may begin with the emergency back-up controlled ventilation 31 subdivision, where the first illustrated supply in this category is oxygen cylinder with toggle handle 144. If oxygen cylinder with toggle handle 144 is present, the individual or system may place an "X" in column 115 indicating the required supply is present.

Column 120, in one embodiment of the present invention, may be designated with a heading of "Functioning Properly?", where the individual or system performing the checklist procedure may place an "X" or other suitable designation in column 120 if the corresponding supply from supply list 110 is functioning properly. For example, the individual or system performing the checklist procedure may check for the extra batteries for laryngoscope 162, where that individual may first check column 115 to verify that the supply is present and if it is present then check column 120 with an "X" if the extra batteries are functioning properly. Alternately, to save time, an individual may simply check column 120 with an "X" after verifying proper function without needing to mark an "X" in column 115 because the supply must be present to be functioning. More generically, if one subsequent passed check (e.g., drug unexpired) implies that other previous checks (such as drug present) have also passed, the previous checks may be bypassed to save time.

Column 125 may be designated with a heading of "Unexpired," where the individual or system performing the checklist procedure may place an "X" or other suitable designation in column 125 if the corresponding supply from supply list 110 has not expired. For example, if the supply of ephedrine 168 in emergency medical kit 30 has not expired, an "X" may be placed in column 125. For supplies that do not have expiration dates such as, for example, stethoscope 156, "not applicable" (N/A) or any other suitable designation may be placed in column 125 next to that item. "N/A" may also be placed in any of columns 115, 120, 125, and 130 when the column is not applicable to the supply found in supply list 110.

Column 130 may be designated with a heading of "Pressurized?", where the individual or system performing the checklist procedure may place an "X" or other suitable designation in column 130 if the corresponding supply from supply list 110 is pressurized. For example, if oxygen cylinder with toggle handle 44 is pressurized, an "X" may be placed in column 130 next to that item.

Figure 4:
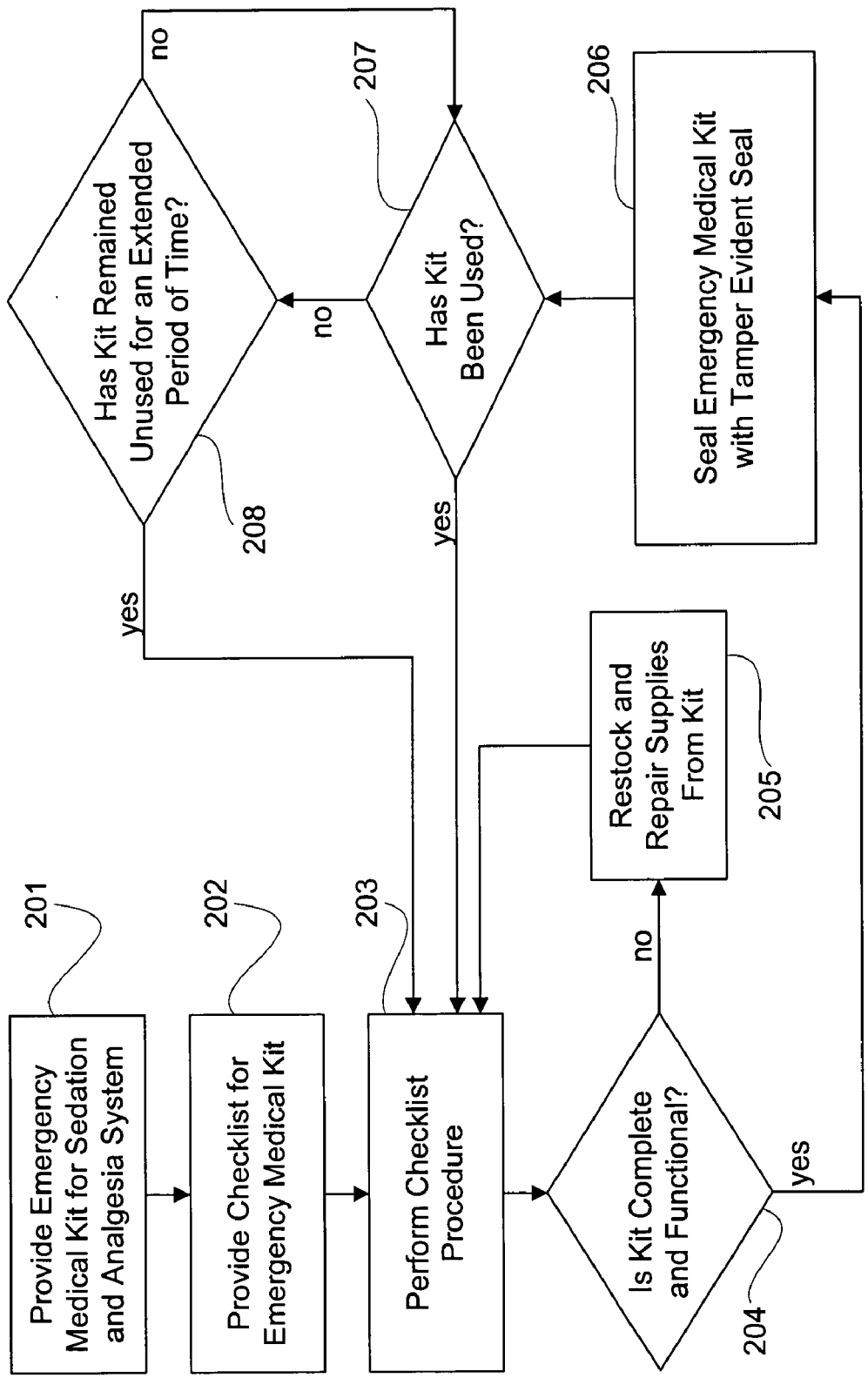
FIG. 4 illustrates a flow chart according to one embodiment of the present invention depicting a method of ensuring the presence and functionality of supplies associated with an emergency medical kit.

FIG. 4 illustrates a particular embodiment of a method 200 for utilizing a resuscitation kit system and pre-use protocols for a sedation and analgesia system according to the present invention. Method 200 comprises step 201, where step 201 comprises providing sedation and analgesia system 22 and emergency medical kit 30, where emergency medical kit 30 is tailored specifically to emergencies that may result from the use of sedation and analgesia system 22. Sedation and analgesia system 22 may be operated in a hospital environment, ambulatory environment, or in any other suitable medical location. Following step 201, method 200 may proceed to step 202.

Step 202 comprises providing checklist 100 for emergency medical kit 30, where checklist 100 comprises a listing of all the required supplies for emergency medical kit 30 and at least one of columns 115, 120, 125, 130 (FIG. 3A), where columns 115, 120, 125, 130 are properly checked before sedation and analgesia system 22 may be operated. Columns 115, 120, 125, 130 may be properly checked when all supplies for emergency medical kit 30 have met all of the applicable requirements. Following step 202, method 200 may proceed to step 203.

Step 203 comprises performing the checklist procedure, where the checklist procedure comprises determining whether each of the supplies for emergency medical kit 30 meets the applicable requirements. For example, drugs associated with emergency medical kit 30 may have to be present and unexpired, where affirmative checks may be placed in column 115 and column 125, yet column 120 and column 130 may not be applicable and may not require an affirmative check or may already be pre-filled with an "N/A" entry. The checklist procedure of step 203 comprises asking the questions presented in columns 115, 120, 125, 130 and notating on checklist 100 with suitable symbols whether the supply from supply list 110 meets the requirements of columns 115, 120, 125, 130, does not meet the requirements of columns 115, 120, 125, 130, or is not applicable. The checklist procedure associated with step 203, in one embodiment of the present invention, is performed following every use of emergency medical kit 30 and following the non-use of emergency medical kit 30 for a predetermined period of time such as, for example, three months. Performing the checklist procedure after every use ensures that drugs have been replenished, unused drugs have not expired, supplies are functional, and gas containers are properly pressurized. Performing the checklist procedure on emergency medical kit 30 following even a period of non-use ensures that expired supplies may be replaced, that degradable or perishable components such as, for example, batteries, may be replaced, and that emergency medical kit 30 is otherwise complete and functional. Following step 203, method 200 may proceed to query 204.

Query 204, in one embodiment of the present invention, comprises ascertaining whether the supplies required for emergency medical kit 30 have complied with all the requirements of checklist 100. If any of the requirements of checklist 100 have not been met, method 200 may proceed to step 205. Step 205 comprises restocking, repairing, and/or replacing components from emergency medical kit 30 to meet the requirements of checklist 100. Following step 205, method 200 may loop back to step 203 where the checklist procedure may again be performed.

Following a "yes" response to query 204, where all supplies required for emergency medical kit 30 have complied with the requirements of checklist 100, method 200 may proceed to step 206. Step 206, in one embodiment of the present invention comprises sealing emergency medical kit 30 with a tamper evident seal (not shown), such as those made by Seton Identification Products, where emergency medical kit 30 may not be opened or the supplies from emergency medical kit 30 removed without the tamper evident seal being broken. The tamper evident seal may be an adhesive tape, plastic clip, or other suitable seal. The tamper evident seal may further carry the date on which the checklist procedure associated with step 203 was performed, who performed the checklist, and/or other suitable information. Checklist 100 may also be affixed to emergency medical kit 30 and/or the tamper evident seal, where the checklist may display the supplies present within emergency medical kit 30, the date the checklist procedure was performed, who performed the checklist, the next date on which the checklist procedure must be performed if emergency medical kit 30 remains unused, and/or any other suitable information. Following step 206, method 200 may proceed to query 207.

Query 207, in one embodiment of the present invention, comprises querying whether emergency medical kit 30 has been used. Query 207 further comprises ascertaining whether the tamper evident seal of emergency medical kit 30 has been broken and/or determining if emergency medical kit 30 has been used. If emergency medical kit 30 has been used or the tamper evident seal has been broken, method 200 may proceed to step 203, where the checklist procedure associated with step 203 must be performed before emergency medical kit 30 may be used. If emergency medical kit 30 has not been used and the tamper evident seal is intact, method 200 may proceed to query 208.

Query 208 comprises querying whether emergency medical kit 30 has remained unused for a pre-determined period of time, where the pre-determined period of time may be, for example, three months, however any suitable time period that ensures drugs or perishable components within emergency medical kit 30 have not expired and that equipment within emergency medical kit 30 is functional is in accordance with the present invention. If the pre-determined time period has elapsed, and emergency medical kit 30 remains unused, method 200 may proceed to step 203. If the pre-determined time period has not elapsed and emergency medical kit 30 remains unused, method 200 may proceed to query 207.

Method 200 ensures that the emergency medical supplies of emergency medical kit 30 will be present, functional, and unexpired in the event that a medical emergency occurs as a result of a procedure involving sedation and analgesia system 22. Method 200 further ensures that emergency medical kit 30 is not tampered with, where if tampering occurs, use of the system occurs, or the system remains unused for a predetermined period of time, that a comprehensive checklist procedure will be performed.

Figure 5:
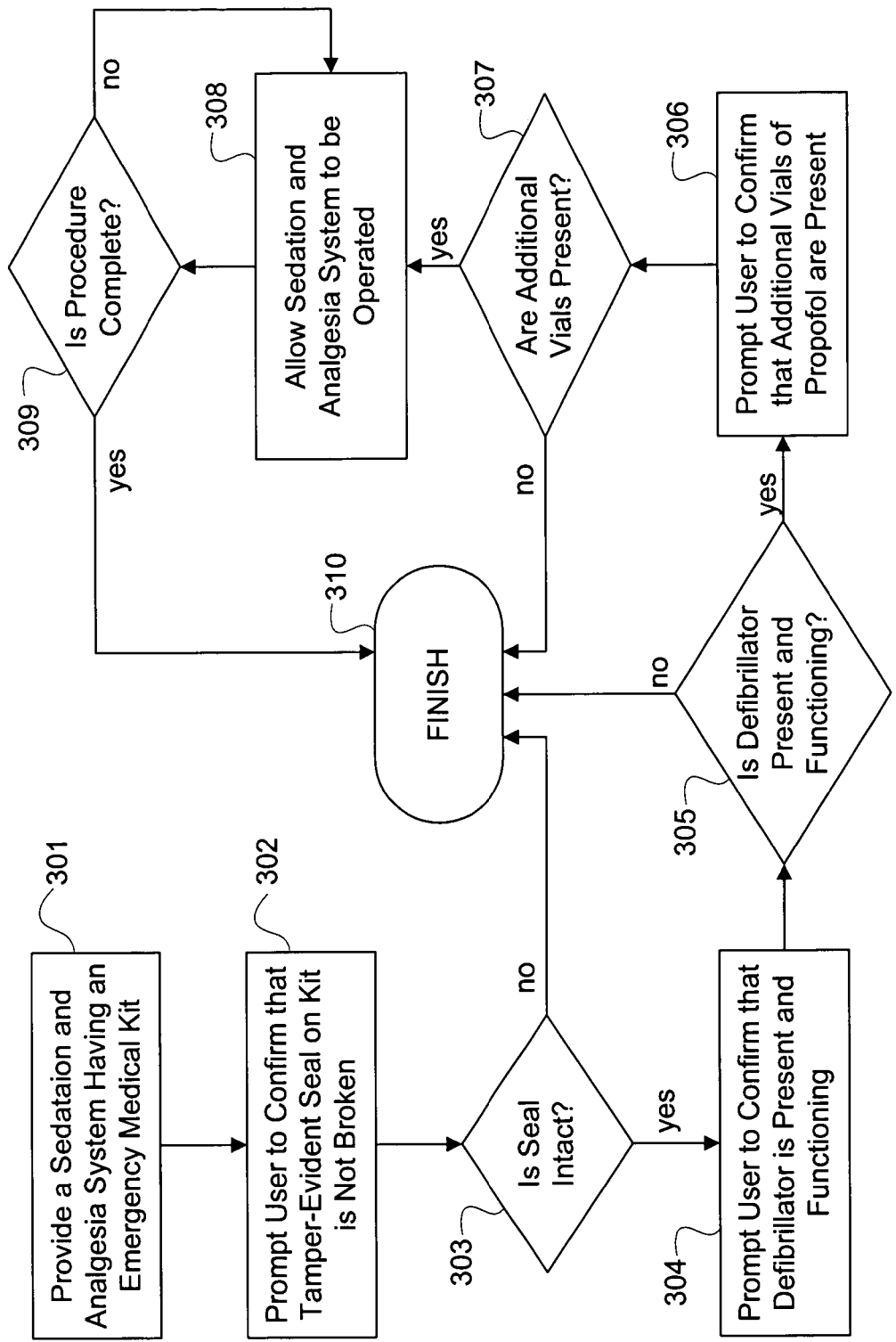
FIG. 5 illustrates a flow chart according to one embodiment of the present invention depicting a method of providing semi-automated pre-use checks to ensure the presence and functionality of components related to an emergency medical kit and a sedation and analgesia system.

FIG. 5 illustrates one embodiment of method 300, where method 300 comprises semi-automated pre-use checks for sedation and analgesia system 22 integrated with emergency medical kit 30. Method 300 comprises step 301, where step 301 comprises providing sedation and analgesia system 22, where sedation and analgesia system 22 is integrated with emergency medical kit 30. Emergency medical kit 30 may be affixed to sedation and analgesia system 22, detachably coupled to sedation and analgesia system 22, or placed in close proximity to sedation and analgesia system 22. Following step 301, method 300 may proceed to step 302.

Step 302 comprises prompting user 13 to confirm that the tamper evident seal (not shown) of emergency medical kit 30 is not broken or is otherwise intact, and that the pre-determined time period of non-use has not elapsed. User 13 may be prompted by user interface 12, where the prompt to confirm the integrity of the seal may be via a touch screen display or any other suitable interface device. Step 302, in one embodiment of the present invention, occurs when sedation and analgesia system 22 is activated, but before drug delivery commences. Prompting user 13 to confirm that the tamper evident seal is intact ensures that the proper checklist procedures were successfully performed in accordance with the checklist procedure of step 203. In an alternative embodiment of the present invention, step 302 may be automated whereby system 22 determines whether an electronically tagged seal is broken or expired. Such a means of electronically tagging a seal and automatically sensing if the seal is invalid is described in U.S. patent application Ser. No. 10/151,255 filed May 21, 3002, and incorporated herein by reference. Following step 302, method 300 may proceed to query 303.

Query 303, in one embodiment of the present invention, comprises querying whether the tamper evident seal of emergency medical kit 30 is intact or the pre-determined time period for non-use has not elapsed. If the answer to query 303 is "no", where the tamper evident seal may have been broken, tampered with, or the pre-determined period of non-use has elapsed, method 300 may proceed to finish 310. Finish 310 comprises disabling sedation and analgesia system 22, where finish 310 prevents drugs from being delivered by sedation and analgesia system 22. Finish 310 further comprises powering down sedation and analgesia system 22 or any other suitable procedure that prevents the administration of drugs by sedation and analgesia system 22. If the response to query 303 is "yes", where the tamper evident seal is intact and the pre-determined time period for non-use has not expired, method 300 may proceed to step 304.

In one embodiment of the present invention, step 304 comprises prompting user 13 to confirm that a defibrillator (not shown) is present and functioning. User 13 may be prompted by a touch screen or other suitable display, where user 13 may use hard buttons, soft buttons, touch screen buttons, or any other suitable means of inputting data to confirm or deny the presence and functionality of the defibrillator. Following step 304, method 300 may proceed to query 305. Query 305 comprises querying whether the defibrillator is present and functioning, where a "no" response to query 305, indicating that the defibrillator is not present or is not functional, may result in method 300 proceeding to finish 310. If the response to query 305 is "yes", where the defibrillator is present and functioning, method 300 may proceed to step 306. Prompting user 13 to confirm the presence of the defibrillator ensures that the defibrillator will be present and in working order before drugs may be administered by sedation and analgesia system 22.

Step 306, in one embodiment of the present invention, comprises prompting user 13 to confirm that additional vials of propofol (or other drugs being administered by system 22) are present, where user 13 may be prompted by user interface 12 in the form of a touch screen or by any other suitable interface device. Following step 306, method 300 may proceed to query 307. Query 307 comprises querying whether additional vials of propofol are present, where a "no" response to query 307, indicating additional vials are not present, may result in method 300 proceeding to finish 310. The present invention further comprises using any suitable drugs in place of, or in cooperation with propofol, where an additional supply of the drug is beneficial. If the response to query 307 is yes, where additional propofol vials are present, method 300 may proceed to step 308. Queries 303, 305, 307, 309 associated with method 300 may be responded to by pressing hard buttons, soft buttons, touch screen buttons, and/or by any other suitable input means.

Step 308 comprises allowing sedation and analgesia system 22 to be operated, where user 13 will be given full access to the drug delivery and patient monitoring features of sedation and analgesia system 22. Method 300 further comprises query 309, where query 309 comprises querying continuously, at certain intervals during, or at specific events during step 308, whether the procedure involving sedation and analgesia system 22 is complete. If the response to query 309 is "yes", where the procedure is complete, method 300 may proceed to finish 310. If the response to query 309 is "no", method 300 may loop back to step 308, where user 13 may continue to operate sedation and analgesia system 22.

Queries 303, 305, 307 are illustrated by way of example only, where user interface 12 of sedation and analgesia system 22 may require user 13 to confirm the presence, functionality, and/or quality of any supplies suitable for use in procedures involving sedation and analgesia system 22. Further, the organization of method 300 is illustrated by way of example only and is not intended to limit the plurality of suitable semi-automated pre-use checks that are in accordance with the present invention. Method 300 ensures that important supplies that may be helpful in performing procedures involving sedation and analgesia system 22 or supplies that may be helpful in the event of a medical emergency involving sedation and analgesia system 22 are present, unexpired, and otherwise functional. Requiring user 13 to input affirmative responses to queries 303, 305, 307 before sedation and analgesia system 22 becomes operable ensures that user 13 has acknowledged and affirmed the presence of critical components related to procedures involving sedation and analgesia system 22 and/or supplies for emergencies that may result from the use of sedation and analgesia system 22.

Further, method 300 provides user 13 with an efficient means of affirming the presence and functionality of emergency medical kit 30. By sealing emergency medical kit 30 with a tamper evident seal following a successful checklist procedure, user 13 must simply note that the tamper evident seal is intact and that the pre-determined period for non-use has not expired to be confident that supplies within the kit are present and functional. Instead of checking for all of the components of emergency medical kit 30 individually, user 13 must simply respond to query 303.

Figure 6:
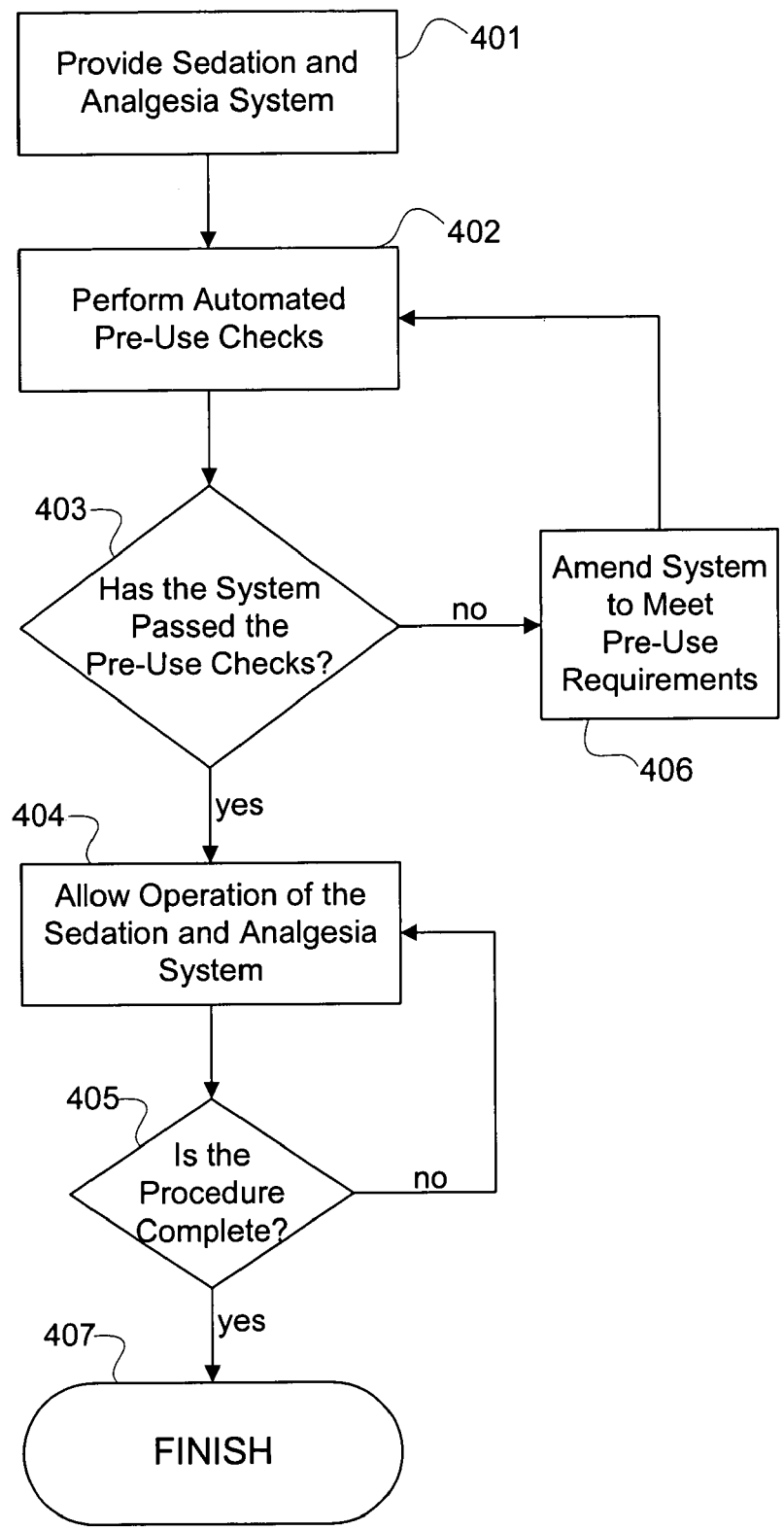
FIG. 6 illustrates a flow chart according to one embodiment of the present invention depicting a method of providing automated pre-use checks to ensure the functionality of a sedation and analgesia system in accordance with the present invention.

FIG. 6 illustrates one embodiment of method 400, where method 400 comprises automated pre-use checks performed by sedation and analgesia system 22 before drug administration associated with sedation and analgesia system 22 commences. Method 400 comprises step 401, where step 401 comprises providing sedation and analgesia system 22. Following step 401, method 400 may proceed to step 402. Step 402 comprises performing automated pre-use checks. Pre-use checks associated with step 402 include checking that the battery (not shown) associated with sedation and analgesia system is charged to a predetermined level such as, for example, 80%, checking that patient information has been entered and that the information is within predetermined safe boundaries for use, checking that there is pressure in oxygen lines, checking the performance of the I.V. purge, checking to be sure that the pulse oximeter and/or the capnometer are reporting respiratory rate, checking that the drug cassette is certified and has not been used, checking for valid drug vials, where the vial is certified and has not been used, and/or checking for the presence of AC power. The present invention further comprises automating any suitable pre-use check such as, for example, by automating semi-automated pre-use checks associated with method 300. Automated pre-use checks may be performed by controller 14, where controller 14 may be programmed to initiate any suitable pre-use check in any suitable order. Following step 402, method 400 may proceed to query 403.

Pre-use checks associated with step 401 further include checks to ensure that emergency medical kit 30 is present and has not sustained an expired period of non-use. In one embodiment of the present invention, the tamper evident seal placed on emergency medical kit 30 may contain embedded RF (radio frequency) technology or other suitable transmission technology. When the tamper evident seal is secured to emergency medical kit 30 following a successful checklist procedure, the tamper evident seal may become active, where sedation and analgesia system 22 may automatically check for the presence of the intact seal during step 401. The tamper evident seal may transmit an RF signal that is powered inductively or by an internal power source such as a battery. In one embodiment of the present invention, the tamper evident seal will not transmit to sedation and analgesia system 22 if the seal is broken or has not been sealed. Once active, the tamper evident seal may further record elapsed time, date of activation, and or any other suitable information, where sedation and analgesia system may receive data from the tamper evident seal pertaining to such parameters in order to ensure that the tamper evident seal is intact and that the predetermined period of non-use for emergency medical kit 30 has not expired. By incorporating embedded RF technology or other transmission technology into the tamper evident seal, the present invention allows for sedation and analgesia system 22 to automatically check for the presence of emergency medical kit 30, automatically check that the predetermined period of non-use for emergency medical kit 30 has not expired, and automatically check that the tamper evident seal is intact and functional. An example of a tamper evident seal having embedded RF technology is described in the Ser. No. 10/151,255 application incorporated above by reference.

Query 403 comprises querying whether sedation and analgesia system 22 has passed the automated pre-use checks associated with step 402. If query 403 is answered "no", where sedation and analgesia system 22 has not passed the pre-use checks, method 400 may proceed to step 406. Step 406 comprises fixing sedation and analgesia system 22, replacing defective components associated with sedation and analgesia system 22, supplying AC power to sedation and analgesia system 22, and/or any other suitable modifications necessary to comply with the automated pre-use checks. Following step 406, method 400 may loop back to step 402, where automated pre-use checks may again be performed. If query 403 is answered "yes", where sedation and analgesia system 22 has passed the automated pre-use checks, method 400 may proceed to step 404.

Step 404 comprises allowing the operation of drug administration features associated with sedation and analgesia system 22, where user 13 is allowed access to drug administration and patient monitoring functionalities. Step 404 further comprises allowing user 13 to operate sedation and analgesia system 22 throughout the duration of a procedure. Following step 404, method 400 may proceed to query 405. Query 405 comprises querying whether the procedure involving sedation and analgesia system 22 is complete. If the response to query 405 is "yes", where the procedure is complete, method 400 may proceed to finish 407. Finish 407 comprises disabling the drug administration and/or monitoring functionality of sedation and analgesia system 22. If the response to query 405 is "no", where the procedure is not complete, method 400 may loop back to step 404.

Automating pre-use checks associated with sedation and analgesia system 22 increases the safety and efficiency of operating sedation and analgesia system 22 as well as procedures involving the use of sedation and analgesia system 22. Automation may reduce the demand on often heavily tasked medical personnel while providing efficient and comprehensive insurance that features associated with sedation and analgesia system 22 are present and operable.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope by the claims as they will be allowed.

The invention claimed is:

1. A sedation and analgesia system comprising:
a patient health monitor device adapted so as to be coupled to a patient undergoing a medical and/or surgical procedure and generate a signal reflecting at least one physiological condition of the patient;
a user interface;
a drug delivery controller supplying one or more drugs to the patient;
a memory device storing a safety data set reflecting parameters of at least one monitored patient physiological condition;
an electronic controller interconnected with the patient health monitor, the user interface, the drug delivery controller, and the memory device storing the safety data set, wherein said electronic controller receives said signal and in response to said signal manages the application of the drugs during said procedure in accord with the safety data set; and
an emergency medical kit, wherein said emergency medical kit is designed to meet the specific needs of medical emergencies related to the delivery of at least one of sedatives, analgesics, and amnestics, and wherein said electronic controller initiates a pre-use check to confirm the presence of said emergency medical kit.

2. The sedation and analgesia system of claim 1, wherein said emergency medical kit is detachably coupled to said sedation and analgesia system.

3. The sedation and analgesia system of claim 1, wherein said emergency medical kit is permanently affixed to said sedation and analgesia system.

4. The sedation and analgesia system of claim 1, wherein said emergency medical kit comprises:
emergency back-up ventilation equipment;
emergency back-up emesis equipment; and
emergency airway management and intubation equipment.

5. The sedation and analgesia system of claim 4, wherein said emergency medical kit further comprises at least one of:
emergency back-up monitoring equipment;
one or more vasopressors;
one or more cardiac rate stimulation drugs;
one or more anaphylaxis treatment drugs;
one or more bronchodilators;
one or more anti-arrhythmia drugs;
one or more myocardial ischemia drugs; and
one or more pharmacological antagonists.

6. The sedation and analgesia system of claim 5, wherein said emergency medical kit further comprises at least one of dextrose, furosemide, intravenous (I.V.) catheters, I.V. tubing, syringes, needles, and alcohol swabs.

7. The sedation and analgesia system of claim 1, wherein said emergency medical kit includes a tamper evident indicia.

8. The sedation and analgesia system of claim 7, wherein said tamper evident indicia uses electronic technology that can be sensed by said sedation and analgesia system.

9. The sedation and analgesia system of claim 8, wherein said sedation and analgesia system automatically senses when said tamper evident indicia is invalid and notifies said user of said invalid indicia.

10. The sedation and analgesia system of claim 9, wherein said electronic technology is embedded radio frequency (RF) technology.

11. The sedation and analgesia system of claim 7, wherein said user interface includes a prompt requiring a user to confirm that said tamper evident indicia is undisturbed and that a pre-determined period of non-use has not elapsed for said emergency medical kit before granting access to said sedation and analgesia system.

12. The sedation and analgesia system of claim 1, wherein said user interface includes an integrated checklist for said emergency medical kit, said checklist comprising a list of required supplies for said emergency medical kit.

13. An apparatus for sedation and/or pain management of a patient undergoing a medical and/or surgical procedure, said apparatus comprising:
a patient health monitor adapted to be coupled to the patient to generate a signal reflecting at least one physiological condition of the patient;
a drug delivery controller supplying a sedative and/or analgesic drug to the patient;
an emergency medical kit containing supplies for resuscitating a patient in the event the patient's condition becomes abnormal; and
an electronic controller containing data reflecting parameters of at least one monitored patient physiological condition, said electronic controller interconnected with the patient health monitor and the drug delivery controller for receiving said signal and managing the drug delivery controller to maintain the patient's physiological condition within the parameters; wherein said electronic controller prompts a user to confirm at least one of that a tamper evident seal of said emergency medical kit is intact and that a pre-determined time period of non-use has not elapsed.

14. The apparatus of claim 13, wherein said emergency medical kit includes a tamper evident indicia, said tamper evident indicia including electronic technology that can be sensed by said apparatus.

15. The apparatus of claim 13, wherein said emergency medical kit includes a tamper evident indicia, and wherein said apparatus automatically senses when said tamper evident indicia is invalid and notifies a user of said invalid indicia.

16. The apparatus of claim 13, wherein said user interface includes a prompt requiring a user to confirm that said tamper evident indicia is undisturbed and that a predetermined period of non-use has not elapsed for said emergency medical kit before granting access to said apparatus.

17. The apparatus of claim 13, further comprising a user interface, wherein said user interface includes a prompt requiring a user to confirm that a tamper evident indicia on said emergency medical kit is undisturbed and that a pre-determined period of non-use has not elapsed for said emergency medical kit before granting access to said apparatus.

18. The apparatus of claim 13, and wherein said electronic controller initiates a pre-use check to confirm the presence and functionality of said emergency medical kit.

19. An apparatus for sedation andlor pain management of a patient undergoing a medical and/or surgical procedure without general anesthesia and/or the presence of an anesthetist, said apparatus comprising:

a patient health monitor adapted to be coupled to the patient to generate a signal reflecting at least one physiological condition of the patient;

a drug delivery controller supplying a sedative and/or analgesic drug to the patient;

a memory device containing data reflecting normal parameters of at least one monitored patient physiological condition;

an electronic controller interconnected with the patient health monitor, the drug delivery controller and with the memory device storing the data and for receiving said signal and managing the drug controller to maintain the patient's physiological condition within normal parameters; and an emergency medical kit interconnected with the electronic controller containing supplies for resuscitating a patient in the event the patient's condition becomes abnormal.

20. The apparatus of claim 19, wherein said emergency medical kit includes a tamper evident indicia.

* * * * *